(12) United States Patent
Honeck et al.

(10) Patent No.: US 7,474,924 B2
(45) Date of Patent: Jan. 6, 2009

(54) JUNCTION FOR MEDICAL ELECTRICAL LEADS

(75) Inventors: Jordon D. Honeck, Maple Grove, MN (US); Gregory A. Boser, Richfield, MN (US); Mark A. Hjelle, White Bear Lake, MN (US); Paul M. Becker, Cedar, MN (US); Scott N. Tuominen, Centerville, MN (US); Michael R. Dollimer, Burnsville, MN (US); Thomas C. Bischoff, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 119 days.

(21) Appl. No.: 10/718,204

(22) Filed: Nov. 20, 2003

(65) Prior Publication Data
US 2005/0113898 A1   May 26, 2005

(51) Int. Cl.
*A61N 1/00* (2006.01)
(52) U.S. Cl. ...................................... 607/122

(58) Field of Classification Search ................. 607/115, 607/116, 119, 122, 123; 365/53
See application file for complete search history.

(56) References Cited

U.S. PATENT DOCUMENTS

| | | | | |
|---|---|---|---|---|
| 3,789,374 | A | * | 1/1974 | Sherman ....................... 365/53 |
| 4,481,953 | A | | 11/1984 | Gold et al. ................... 128/786 |
| 5,522,872 | A | | 6/1996 | Hoff ............................. 607/119 |
| 5,676,694 | A | * | 10/1997 | Boser et al. .................. 607/122 |
| 6,016,436 | A | * | 1/2000 | Bischoff et al. ............. 600/374 |
| 6,181,971 | B1 | | 1/2001 | Doan ........................... 607/116 |
| 6,259,954 | B1 | | 7/2001 | Conger et al. ............... 607/122 |
| 6,505,401 | B1 | | 1/2003 | Doan ........................... 29/860 |

* cited by examiner

*Primary Examiner*—George Manuel
(74) *Attorney, Agent, or Firm*—Carol F. Barry

(57) ABSTRACT

A medical electrical lead includes a conductive component coupling a coil to a wire or cable; the conductive component includes a first side, a second side, a first groove formed in the first side and a second groove formed in the second side. The first groove holds a portion of the cable and the second groove holds a portion of the coil.

35 Claims, 9 Drawing Sheets

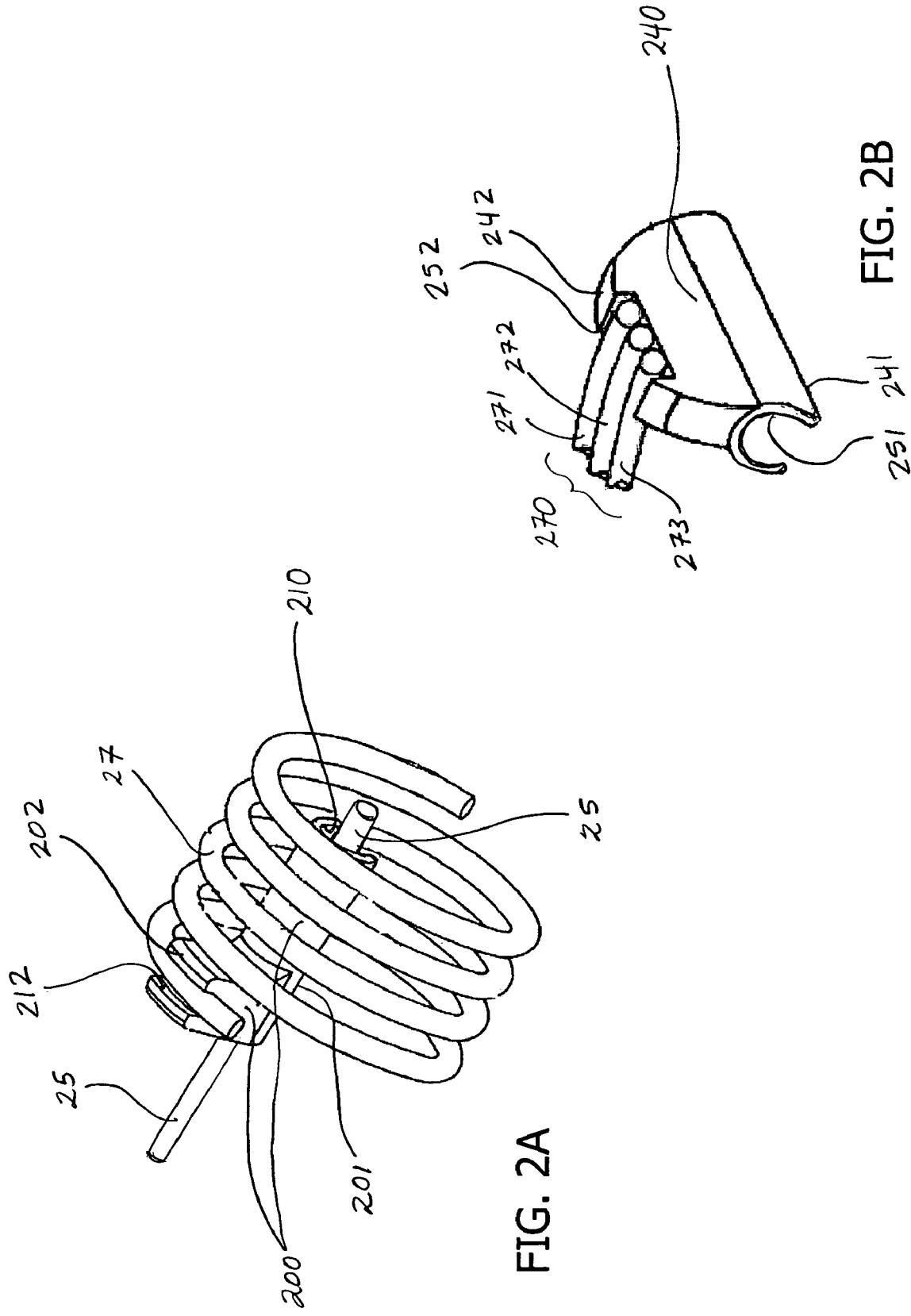

JUNCTION FOR MEDICAL ELECTRICAL LEADS

TECHNICAL FIELD

The present invention relates to medical electrical leads and more particularly to junctions included in such leads.

BACKGROUND

Cardiac stimulation systems commonly include a pulse-generating device, such as a pacemaker or implantable cardioverter/defibrillator that is electrically connected to the heart by at least one electrical lead. An electrical lead delivers electrical pulses emitted by the pulse generator to the heart, stimulating the myocardial tissue via electrodes included on the lead. Furthermore, cardiac signals may be sensed by lead electrodes and conducted, via the lead, back to the device, which also monitors the electrical activity of the heart.

Medical electrical leads are typically constructed to have the lowest possible profile without compromising functional integrity, reliability and durability. Often junctions formed between a conductor and other components included in leads, for example electrodes, can increase the lead's profile, therefore it is desirable to develop low profile junctions.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and:

FIGS. 2A-B are perspective views of junctions according to alternate embodiments of the present invention;

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1:
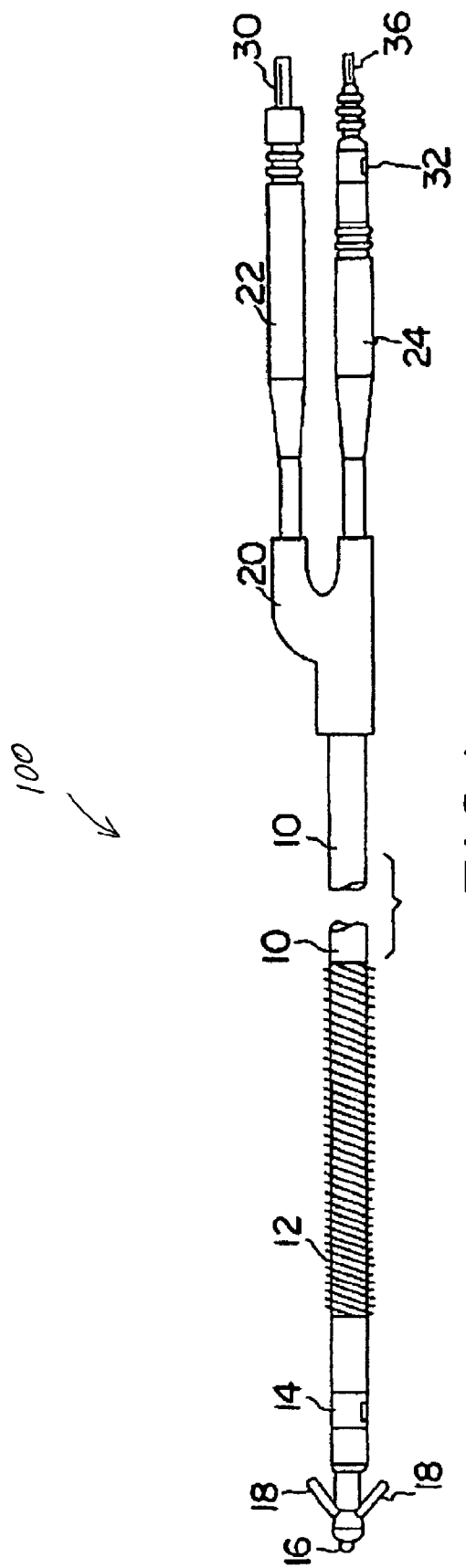
FIG. 1 is a plan view of an exemplary medical electrical lead in which embodiments of the present invention may be incorporated.

FIG. 1 is a plan view of an exemplary medical electrical lead 100 in which embodiments of the present invention may be incorporated. FIG. 1 illustrates lead 100 including a lead body 10 extending distally from a transition sleeve 20 to a distal end, which includes an electrode tip 16, tines 18 and an electrode ring 14; a defibrillation coil extends along a portion of lead body 10 in proximity to the distal end. FIG. 1 further illustrates connector legs 22 and 24, which are adapted to couple lead to an medical device according to means well known to those skilled in the art, extending proximally from transition sleeve 20; conductors (not shown) extending through lead body 10, transition sleeve 20 and legs 24, 22 couple electrodes 16, 14 and 12 to connector contacts 36, 32 and 30, respectively, of connector legs 24 and 22. Embodiments of the present invention include means for coupling a conductive coil, for example defibrillation electrode 12, to a conductive wire or cable, for example the conductor extending within lead body coupling electrode 12 to connector contact 30.

FIGS. 2A-B are perspective views of junctions according to alternate embodiments of the present invention. FIG. 2A illustrates a conductive component 200 including a first groove 210 formed in a first side 201 and a second groove 212 formed, approximately perpendicular to first groove 210, in a second side 202; a portion of a conductive wire or cable 25 is held in first groove 210 and a portion of a conductive coil 27 is held in second groove 212. According to embodiments of the present invention coil 27 and wire or cable 25 are electrically and mechanically coupled by means of such junctions, i.e. wire or cable 25 in first groove 210 and coil 27 in second groove 212, formed by conductive component 200; coil 27 may function as an electrode, i.e. defibrillation electrode 12 illustrated in FIG. 1, or may function as a conductor enclosed within a lead body. FIG. 2B illustrates a portion of a multifilar conductive coil 270 held within a second groove 252 formed in a second surface 242 of a conductive component 240 according to an alternate embodiment of the present invention. FIG. 2B further illustrates conductive component 240 including a first groove 251 formed in a first side 241 which is adapted to hold a conductive wire or cable, i.e. wire or cable 25 illustrated in FIG. 2A. In the context of the present invention, it should be understood that the term "conductive wire or cable" covers conductors including portions that lay approximately straight or approximately aligned with a first groove, i.e. grooves 210, 251, of a conductive component, i.e. components 200, 240.

Figure 3A:
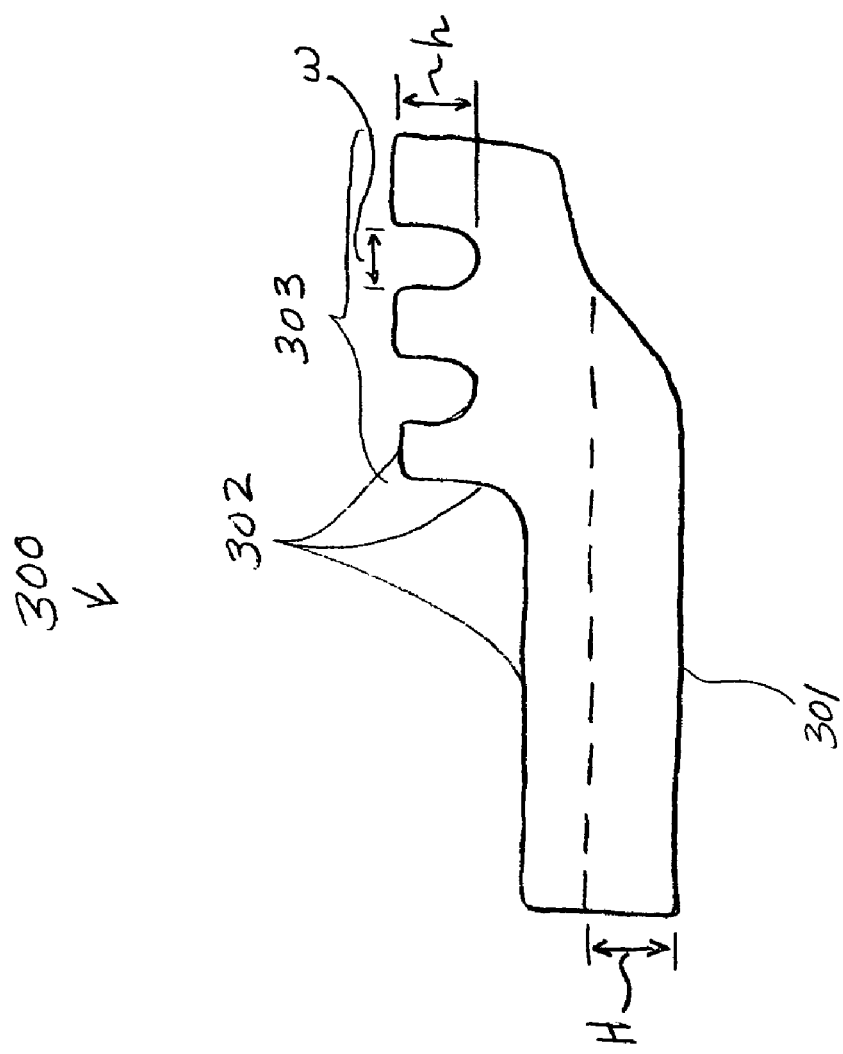
FIG. 3A is a plan view of a conductive component according to one embodiment of the present invention.
Figure 3B:
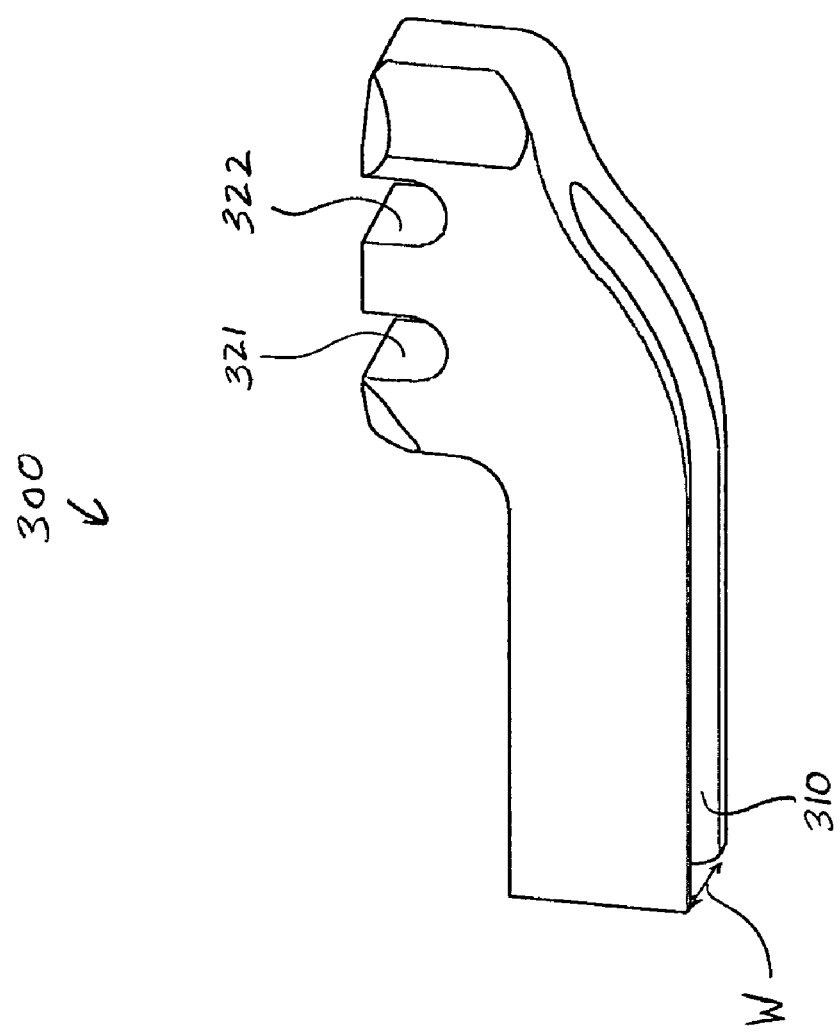
FIG. 3B is a perspective view of the component illustrated in FIG. 3A.

FIG. 3A is a plan view of a conductive component 300 and FIG. 3B is a perspective view of the component according to one embodiment of the present invention. FIGS. 3A-B illustrate conductive component 300 including a first groove 310 formed in a first side 301 and a plurality of grooves 321, 322 formed in a protruding surface 303 of a second side 302. Conductive component 300 may be formed of any conductive biocompatible material, examples of which include but are not limited to titanium, stainless steel, tantalum and platinum. According to one exemplary embodiment of the present invention, a width W of first groove 310 is approximately 0.007 inch to approximately 0.0085 inch, to accommodate a wire or cable of approximately 0.0065 inch in diameter, and a width w of grooves 321, 322 is approximately 0.007 inch to approximately 0.01 inch to accommodate individual coil filars having diameters of approximately 0.007 inch. Furthermore, according to the exemplary embodiment, a height H of first groove 310 is approximately 0.0115 inch to approximately 0.0135 inch and a height h of grooves 321, 322 is approximately 0.007 inch to approximately 0.009 inch.

Figure 4:
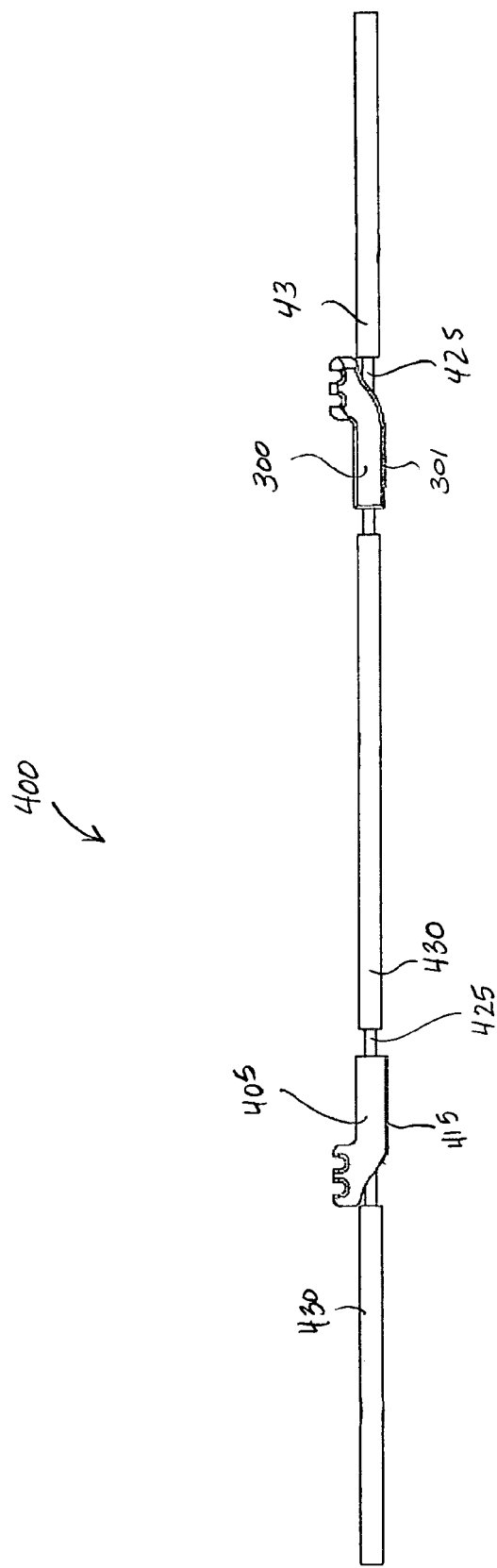
FIG. 4 is a plan view of a subassembly according to one embodiment of the present invention.

FIG. 4 is a plan view of a subassembly 400 according to one embodiment of the present invention. FIG. 4 illustrates subassembly 400 including conductive component 300 and a second conductive component 406 each fitted onto a separate portion of a conductive wire or cable 425. FIG. 4 further illustrates wire or cable 425 including an insulative outer layer 430, which has been removed from the portions held in components 300, 405. According to embodiments of the present invention components 300, 405 may be fitted onto wire or cable 425 by assembling wire or cable 425 into a first groove of components 300, 405 (reference FIG. 3B, first groove 310) from first sides 301, 415, respectively, therefore a groove width, for example width W illustrated in FIG. 3B, need not accommodate a larger diameter formed by outer layer 430.

According to the exemplary embodiment first described in conjunction with FIGS. 3A-B, wire or cable 425 includes nineteen cabled wire strands, each formed of an MP35N alloy, divided up into a center strand, six intermediate peripheral strands and twelve outer peripheral strands; each strand of both sets of peripheral strands includes a silver core. According to this embodiment, the center strand has a diameter of approximately 0.0014 inch, the intermediate peripheral strands have a diameter of approximately 0.0013 inch, a left hand lay and a pitch of approximately 0.044 inch, and the outer peripheral strands have a diameter of approximately 0.0012 inch, a right hand lay and a pitch of approximately 0.064 inch. Furthermore, according to this embodiment, a coating of ETFE fluoropolymer forms outer layer 430; outer layer 430 may be removed from portions to be fitted into components 300, 405 by $CO_2$ laser ablation or by cutting with a scalpel.

Figure 5B:
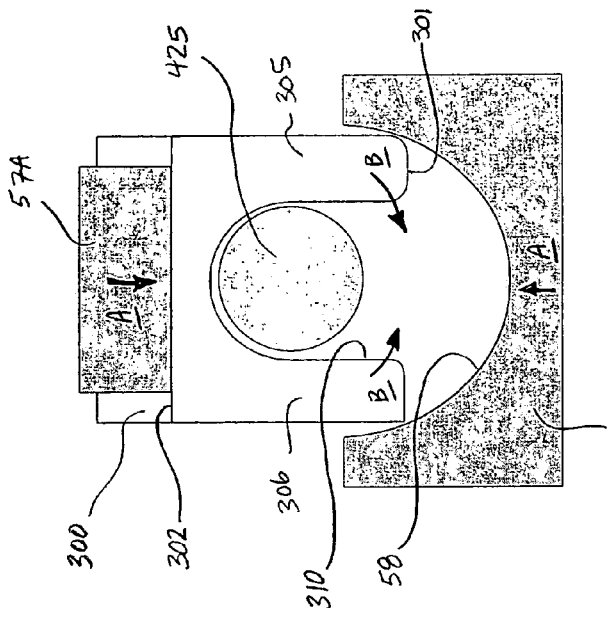
FIGS. 5A-C are end view schematics depicting of means for coupling according to alternate embodiments of the present invention.
Figure 5C:
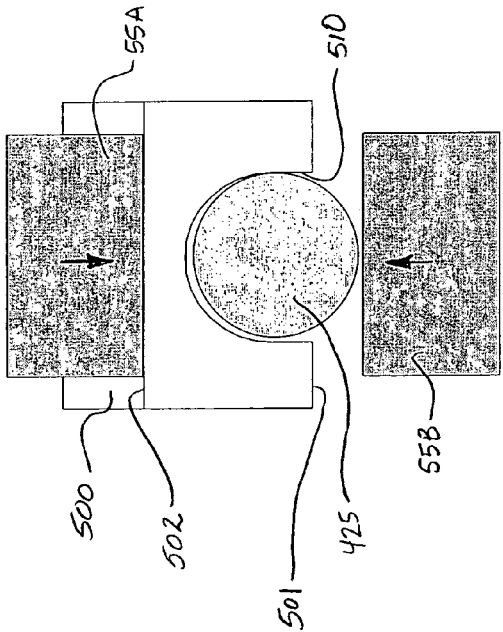
Figure 5A:
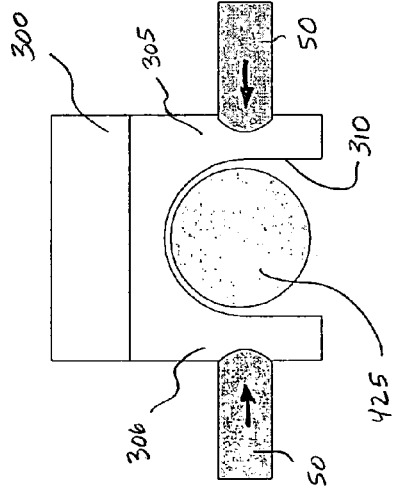

FIGS. 5A-C are end view schematics depicting of means for coupling according to alternate embodiments of the present invention. According to embodiments of the present invention, a conductive component, i.e. component 300, couples a portion of a conductive wire or cable, i.e. wire or cable 425, via a crimp formed as illustrated in either FIG. 5A or 5B. FIG. 5A illustrates first groove 310 of conductive component 300 holding conductive wire or cable 425 and crimping or indenting heads 50 directed per arrows into side walls 305 and 306. FIG. 5B also illustrates first groove 310 of conductive component 300 holding conductive wire or cable 425, but a crimp is formed according to this embodiment by crimping heads 57A and 57B directed per arrows A against first side 301 and second side 302. FIG. 5B further illustrates crimping head 57B including a contoured surface 58 which when pressed against first side 301 forces portions of side walls 305 and 306 in proximity to first side, per arrows B, to deform inwardly, beneath wire or cable 425. According to alternate embodiments of the present invention, a conductive component 500 couples a portion of wire or cable 425 via a resistance weld formed as illustrated in FIG. 5C. FIG. 5C illustrates a first groove 510 of conductive component 500 holding conductive wire or cable 425 and resistance welding heads 55A, 55B directed per arrows toward surfaces 502 and 501. FIG. 5B further illustrates that lower welding head 55B will be stopped by surface 501, preventing crushing of cabled configuration of wire or cable 425 as pressure is applied between heads 55A, 55B during welding; such a configuration for resistance welding is disclosed in commonly assigned co-pending patent application entitled "Novel Welded Junction for Medical Electrical Leads", which is incorporated by reference herein in its entirety. According to yet another alternate embodiment laser welding is employed to couple wire or cable 425 to component 500.

Figure 6:
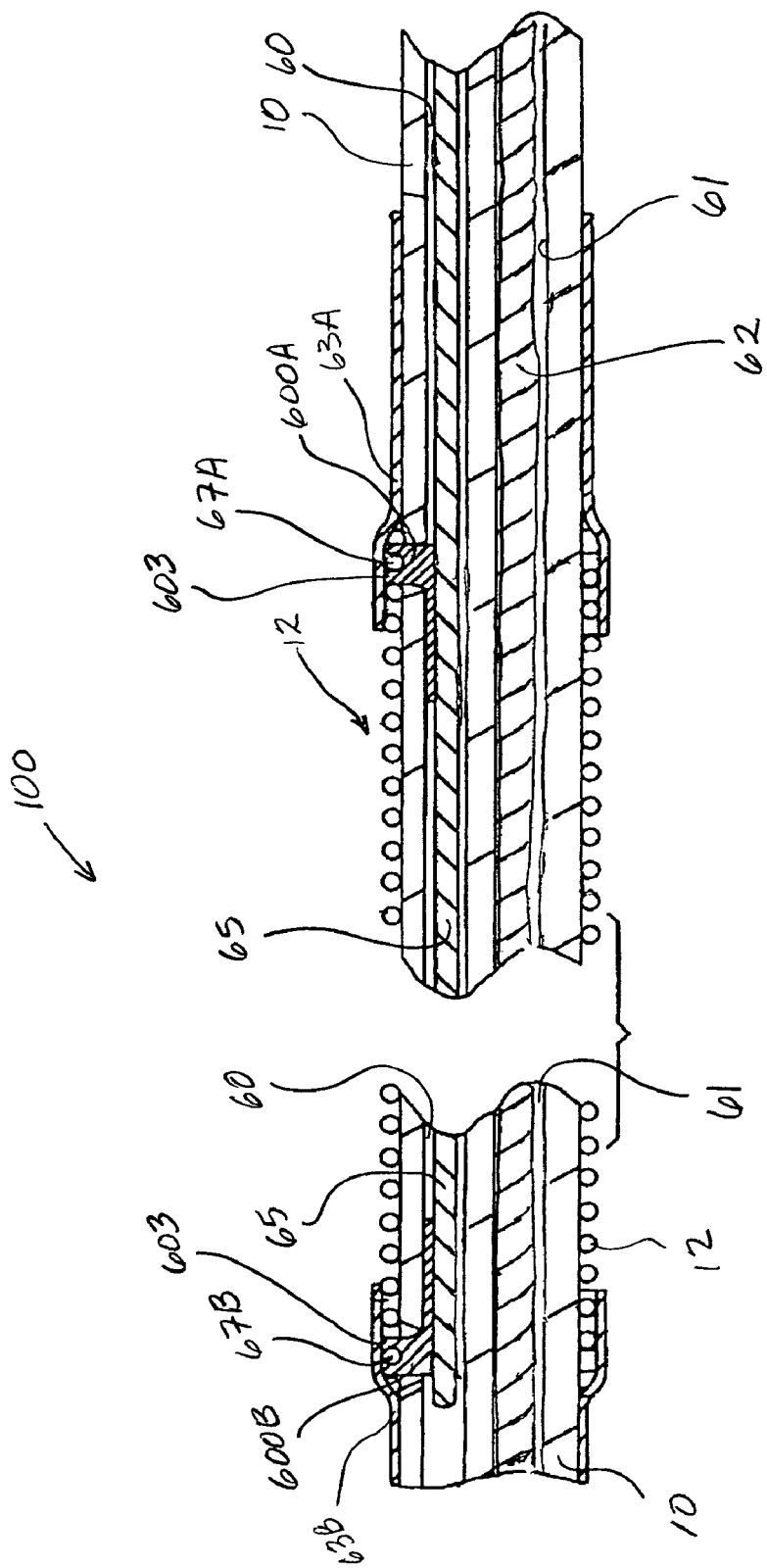
FIG. 6 is an axial section view of a portion of the lead illustrated in FIG. 1 including a junction according to one embodiment of the present invention.

FIG. 6 is an axial section view of a portion of the lead illustrated in FIG. 1 including two junctions according to one embodiment of the present invention. FIG. 6 illustrates lead body 10 formed in part by an insulative polymer multi-lumen tubing, wherein a wire or cable 65, coupled to conductive components 600A and 600B, extends within a first lumen 60, and a coil conductor 62 extends within a second lumen 61 coupling tip electrode 16 to connector contact 36 (FIG. 1). According to some embodiments, a coupling of wire or cable 65 with conductive components 600A, 600B is completed outside lead body 10, resulting in a subassembly similar to subassembly 400 illustrated in FIG. 4 and as described in conjunction with FIG. 5A, 5B or 5C; then the assembly of wire or cable 65 and components 600A, 600B is inserted into first lumen 60 and positioned such that a protruding surface 603 of each component 600A, 600B extends through an outer surface of lead body 10 to couple with a portion of a coil 67A, 67B, respectively, which extends around the outer surface of lead body 10 to form defibrillation electrode 12. According to an exemplary embodiment, electrode 12 is formed from a tantalum cored platinum material, components 600A, 600B are formed from tantalum, and the multi-lumen tubing is formed of silicone. Although FIG. 6 illustrates conductive components 600A, 600B positioned for coupling at either end of defibrillation coil 12, alternate embodiments include those employing a single conductive component coupling a conductive wire or cable to a conductive coil at a point that may be any where along a length of the coil.

FIG. 6 further illustrates polymer sleeves 63A and 63B covering protruding surfaces 603; sleeves 63A, 63B may be formed of any biocompatible insulative polymer examples of which include silicone and polyurethane. According to the illustrated embodiment, sleeves 63A, 63B serve to seal first lumen 60 by covering an opening in lead body 10, which was created to allow protruding surfaces 603 to pass through the outer surface of lead body 10; an adhesive backfill, for example comprising silicone medical adhesive, under sleeves 63A, 63B and around protruding surfaces 603 may also be incorporated. According to an alternate embodiment the adhesive backfill alone may serve to seal first lumen 60 without the need for sleeves 63A, 63B.

Figure 7B:
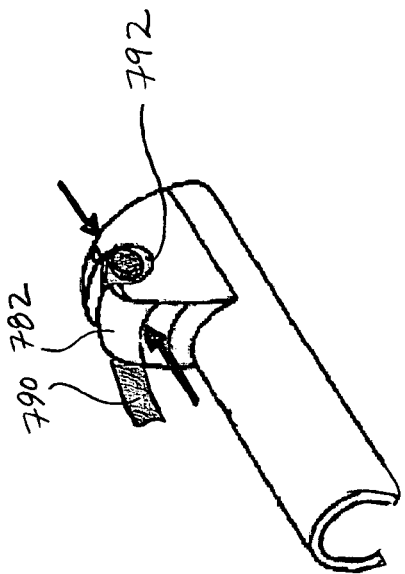
FIGS. 7A-B are perspective view schematics depicting further means for coupling according to alternate embodiments.
Figure 7A:
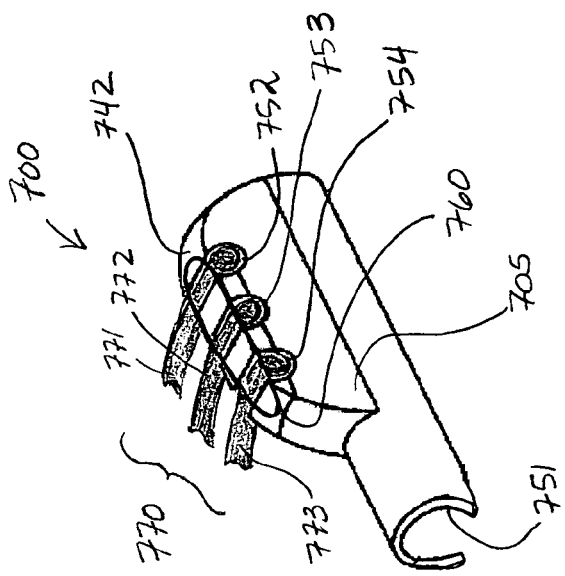

FIGS. 7A-B are perspective view schematics depicting further means for coupling according to alternate embodiments. FIG. 7A illustrates an assembly 700 including a multi-filar conductive coil 770 and a conductive component 705 wherein a portion of each coil filar 771, 772 and 773 is held within a groove 752, 753 and 754, respectively, which are formed in a protruding surface 742 (a conductive wire or cable is not shown within a groove 751 for the sake of simplicity). According to one embodiment of the present invention, portions of filars 771, 772 and 773 are welded to conductive component 705 in circled area 760 according to any appropriate method known to those skilled in the art. According to an alternate embodiment, as illustrated in FIG. 7B, a crimp per arrows couple a portion of a conductive coil 790, which is held within groove 792 formed in protruding surface 782, to a conductive component 785 to form an assembly 780. Conductive coils 770, 790 may be formed of any conductive biocompatible material, examples of which include but are not limited to titanium, stainless steel, tantalum and platinum.

Figure 8:
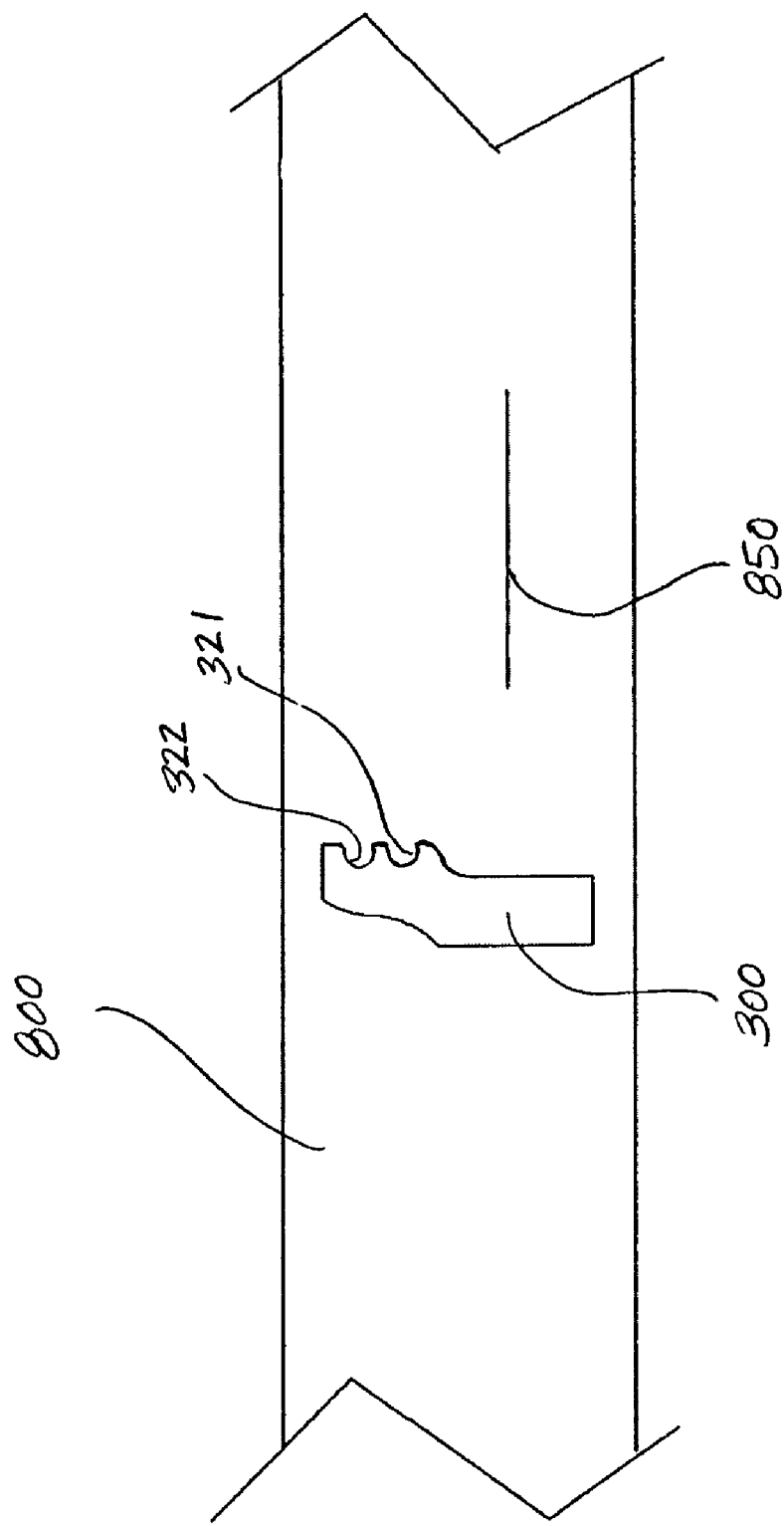
FIG. 8 is a top view schematic depicting a means for forming a conductive component according to one embodiment of the present invention.

FIG. 8 is a top view schematic depicting a means for forming a conductive component according to one embodiment of the present invention. FIG. 8 illustrates a portion of a length of strip stock 800 from which conductive component 300

(FIGS. 3A-B) is stamped. According to the illustrated embodiment a grain orientation of strip stock 800 is oriented per line 850 with respect to a profile of component 300, which includes second grooves 321 and 322. According to one exemplary embodiment a single stage stamping technique followed by an EDM machining process, to form first groove 310 (FIG. 3B), forms component 300 from a fully annealed tantalum material of the purest grade, for example tantalum according to ASTM F560. Alternate embodiments of conductive components are formed by other combinations of machining and stamping processes, machining processes alone, multi-stage stamping or any other appropriate method known to those skilled in the art.

In the foregoing detailed description, the invention has been described with reference to specific embodiments. However, it may be appreciated that various modifications and changes can be made without departing from the scope of the invention as set forth in the appended claims.

What is claimed is:

1. A medical electrical lead, comprising:
   an elongate lead body;
   a conductive coil extending along a portion of the lead body;
   conductive wire or cable extending along a portion of the lead body, the conductive wire or cable comprising an insulative outer layer having an outer diameter, the insulative outer layer removed along a segment of the wire or cable to form an uninsulated portion; and
   a conductive component coupling the coil to the wire or cable and including a first side, a second side opposing the first side, a first sidewall extending from the first side to the second side and a second side wall opposing the first side wall and extending from the first side to the second side, a first groove formed in the first side between the first side wall and the second side wall and having an open side extending along the first side and between the first side wall and the second side wall for receiving the uninsulated portion of the wire or cable, and a second groove formed in the second side;
   wherein the first groove holds the uninsulated portion of the wire or cable extending directly through the first groove and the second groove holds a portion of the coil, the first groove having a groove width smaller than the outer diameter of the insulative outer layer.

2. The lead of claim 1, wherein the second side includes a protruding surface in which the second groove is formed.

3. The lead of claim 2, further comprising:
   a lumen disposed within the lead body wherein the wire or cable extends within the lumen of the lead body;
   the coil extends around an outer surface of the lead body; and
   the first side of the conductive component is positioned within the lumen of the lead body and the protruding surface of the second side of the conductive component extends through the outer surface of the lead body.

4. The lead of claim 1, wherein the wire or cable includes a proximal portion and a distal portion, the proximal portion extending proximally from the portion held in the first groove and the distal portion extending distally from the portion held in the first groove.

5. The lead of claim 4, wherein the proximal and distal portions of the wire or cable each include an insulative outer layer.

6. The lead of claim 1, wherein
   the portion of the wire or cable is connected within the first groove by indentation of the first side wall and the second side wall.

7. The lead of claim 1, wherein
   the portion of the wire or cable is connected within the first groove by inward deformation of portions of the first side wall and the second side wall in proximity to the first side.

8. The lead of claim 1, wherein the portion of the wire or cable is connected within the first groove.

9. The lead of claim 1, wherein the second groove includes a plurality of grooves.

10. The lead of claim 9, wherein the portion of the coil includes a plurality of filars, each of which is held within a one of the plurality of grooves.

11. The lead of claim 10, wherein each of the plurality of filars is welded within a one of the plurality of grooves.

12. The lead of claim 1, wherein another portion of the coil forms a defibrillation electrode.

13. The lead of claim 1, wherein the component is formed from a length of strip stock by a stamping process.

14. The lead of claim 1, wherein the component includes a grain orientation approximately perpendicular to the first groove.

15. The lead of claim 1, wherein the component is formed of a material comprising tantalum.

16. The lead of claim 1, wherein the second groove extends approximately perpendicular to the first groove.

17. The lead of claim 1, wherein the portion of the coil includes a plurality of filars.

18. The lead of claim 17, wherein the plurality of filars are welded within the first groove.

19. The lead of claim 1 wherein the component is formed of a material comprising platinum.

20. The lead of claim 1, wherein the component is formed of a material comprising stainless steel.

21. The lead of claim 1, wherein the component is formed of a material comprising titanium.

22. The lead of claim 1, wherein the first groove is formed by an EDM process.

23. A component coupling a conductive wire or cable to a conductive coil of a medical electrical lead, comprising:
    a first side including a first groove formed therein;
    a second side opposing the first side and including a second groove formed therein;
    a first side wall extending from the first side to the second side; and
    a second side wall opposing the first side wall and extending from the first side to the second side,
    the first groove formed in the first side between the first side wall and the second side wall and having an open side having a first groove width extending along the first side and between the first side wall and the second side wall for receiving an uninsulated portion of the conductive wire or cable,
    wherein the first groove is adapted to hold athe uninsulated portion of the conductive wire or cable extending directly through the first groove and the second groove is adapted to hold a portion of the conductive coil, the first groove width being smaller than an outer diameter of an insulated portion of the conductive wire or cable.

24. The component of claim 23, wherein the second side includes a protruding surface in which the second groove is formed.

25. The component of claim 23, wherein the component is formed from a length of strip stock.

26. The component of claim 23, further comprising a grain orientation approximately perpendicular to the first groove.

27. The component of claim 23, wherein the component is formed from a material comprising tantalum.

28. The component of claim 23, wherein the second groove extends approximately perpendicular to the first groove.

29. The component of claim 23, wherein the second groove includes a plurality of grooves.

30. The component of claim 23, wherein the component is formed of a material comprising platinum.

31. The component of claim 23, wherein the component is formed of a material comprising stainless steel.

32. The component of claim 23, wherein the component is formed of a material comprising titanium.

33. The component of claim 23, wherein the first groove is formed by an EDM process.

34. A medical electrical lead, comprising:
   an elongate lead body;
   a conductive coil extending along a portion of the lead body;
   a conductive wire or cable extending along a portion of the lead body and having an outer insulating layer having a first outer diameter, the outer insulating layer removed along a portion of the wire or cable forming an uninsulated portion, the uninsulated portion having a second outer diameter; and
   a conductive component coupling the coil to the wire or cable and comprising:
   a first side,
   a second side opposing the first side,
   a first side wall, extending from the first side to the second side,
   a second side wall opposing the first side wall and extending from the first side to the second side,
   a first groove formed in the first side between the first side wall and the second side wall and having a width along the first side defined by the first side wall and the second side wall for receiving a portion of the wire or cable from the first side;
   and a second groove formed in the second side;
   wherein the uninsulated portion of the wire or cable extends directly through the first groove and a portion of the coil extends through the second groove,
   the width of the first groove being smaller than the first outer diameter of the outer insulating layer,
   the uninsulated portion of the wire or cable held within the first groove by inward deformation of the first side wall toward the second side wall along the first side.

35. The medical electrical lead of claim 34 wherein the first groove having a height that is greater than the second outer diameter of the uninsulated portion of the wire or cable.

* * * * *